(12) United States Patent
Takhtalian et al.

(10) Patent No.: US 6,231,836 B1
(45) Date of Patent: May 15, 2001

(54) FOLIC ACID DENTIFRICE

(76) Inventors: Robert Takhtalian; Yvonne M. Takhtalian, both of 7141 S. Valley View, Las Vegas, NV (US) 89118

( * ) Notice: Subject to any disclaimer, the term of this patent is extended or adjusted under 35 U.S.C. 154(b) by 0 days.

(21) Appl. No.: 09/477,300

(22) Filed: Jan. 4, 2000

Related U.S. Application Data

(60) Provisional application No. 60/143,386, filed on Jul. 12, 1999.

(51) Int. Cl.⁷ ............... A61K 7/16; A61K 7/24; A61K 7/26
(52) U.S. Cl. ............... 424/49; 424/55; 424/58
(58) Field of Search .......................... 424/49–58

(56) References Cited

U.S. PATENT DOCUMENTS

| | | | | |
|---|---|---|---|---|
| 4,272,512 | * | 6/1981 | Gaffar | 424/49 |
| 4,335,110 | * | 6/1982 | Collins | 424/145 |
| 4,376,115 | * | 3/1983 | McCorey | 424/145 |
| 4,469,674 | * | 9/1984 | Shah et al. | 424/52 |
| 4,683,133 | * | 7/1987 | Southard | 424/49 |
| 5,066,483 | * | 11/1991 | Harkrader et al. | 424/54 |
| 5,817,297 | * | 10/1998 | Ha et al. | 424/58 |
| 5,925,335 | * | 7/1999 | Shuch et al. | 424/49 |

* cited by examiner

*Primary Examiner*—Shep K. Rose
(74) *Attorney, Agent, or Firm*—Robert Ryan Morishita; Anderson & Morishita

(57) ABSTRACT

A non-alcoholic dentifrice for controlling gum disease and bad breath includes natural constituents such as nutrients which aid in cell reproduction, immunity, and wound healing and herbal supplements having anti-bacterial and anti-inflammatory properties. An optional embodiment of the solution includes approximately 10% by mass folic acid, 10% by mass zinc, 25% by mass myrrh oil, 25% by mass clove oil, and 30% by mass water. A single dose of five milliliters includes approximately 0.5 milligrams folic acid, 0.5 milligrams zinc, 1.25 milligrams myrrh oil, 1.25 milligrams clove oil, and 1.5 milligrams water.

5 Claims, No Drawings

FOLIC ACID DENTIFRICE

RELATED APPLICATION DATA

The present application claims priority to provisional application Ser. No. 60/143,386 filed Jul. 12, 1999 by Applicants herein.

FIELD OF THE INVENTION

The present invention relates to solutions for cleaning the teeth and gums. Specifically, the present invention is a non-alcoholic dentifrice for controlling inflammation and infection of the gums, inhibiting bacterial growth, controlling bad breath, and encouraging wound healing, immunity, and tissue growth of the teeth and gums.

BACKGROUND OF THE INVENTION

Medical studies estimate that as many as 75% of adults in the United States suffer from some form of gum disease. This is a significant medical problem because, in its advance stages, gum disease can cause teeth to loosen and, eventually, fall out. Thus, gum disease is believed to be a leading cause of tooth loss.

Among gum diseases, gingivitis is the most common. Gingivitis is caused by a buildup of bacteria on the teeth and gums. In its early stages, gingivitis causes minor symptoms such as bad breath, bleeding, and sensitivity of the gums. However, in its advanced stages, the gingivitis-causing bacteria cause swelling and irritation of the gums and can lead to more severe forms of periodontal disease.

For example, gingivitis-causing bacteria in plaque between the teeth and gums can, if left untreated, cause infection of the gums. This infection can damage the tooth and gum tissue causing loosening of the teeth. As the teeth loosen, further buildup of bacteria-infested plaque occurs. This self-reinforcing cycle eventually causes the loose teeth to loosen to the point that they fall out or require extraction.

The most commonly recommended preventative for gum disease is regular flossing and brushing of the teeth. Brushing and flossing cleans food and other material from the teeth and prevents a buildup of plaque and bacteria. Dentists also recommend annual or semi-annual visits to a dentist for examination and professional tooth cleaning.

The drawback to these methods are that the toothpastes used are typically not made from natural ingredients but may include synthetic chemicals. Further, brushing and flossing may not reach all the surfaces of the teeth. For example, the rear surfaces of the back teeth may not be effectively cleaned. Likewise, a common place for bacterial buildup is along loose fillings or crowns which cannot be cleaned with floss or a toothbrush.

Alternatively or additionally, mouthwashes may be used to prevent gum disease and bad breath. Mouthwashes are typically solutions containing, as their active ingredient, alcohol to kill the bacteria which cause gum disease. These mouthwashes are usually effective in killing the bacteria and in reaching areas which are difficult or impossible to reach with a toothbrush or floss.

However, mouthwashes which include alcohol can cause other dental problems. Specifically, alcohol in the mouthwash can cause a dry mouth which can result in laryngitis and swallowing difficulties. More importantly, because the teeth are not properly lubricated, a dry mouth can allow food to stick to the teeth. Thus, the frequent use of mouthwashes may actually contribute to plaque buildup.

It can be seen, therefore, that there is a need in the art for a product, and a process for making a product, for rinsing the mouth which can clean the surfaces of the teeth and kill bacteria on all the exposed areas of the teeth using natural constituents without the side effects caused by alcohol.

SUMMARY OF THE INVENTION

A dentifrice, either a mouthwash solution or a toothpaste, includes nutritional supplements which aid in cell reproduction, immunity, and wound healing and herbal supplements having anti-bacterial properties and anti-inflammatory properties. According to an embodiment of the present invention, a solution is made which includes the nutrients zinc and folic acid and the herbal supplements clove oil and myrrh oil. In an optional embodiment, the solution includes 25% by mass clove oil, 25% by mass myrrh oil, 10% by mass folic acid, 10% by mass zinc, and 30% by mass water. In such an optional embodiment, 5 milliliters of solution optionally includes 0.5 milligrams zinc, 0.5 milligrams folic acid, 1.25 milligrams clove oil, 1.25 milligrams myrrh oil and 1.5 milligrams water.

The solution is made using powdered zinc and liquid folic acid, myrrh oil, and clove oil. The manufacture takes place at ambient pressure and room temperature. The toothpaste embodiment may additionally include a thickening agent to give a paste-like consistency.

In use, a user pours a dose into the user's mouth and swishes vigorously for between thirty and sixty seconds. The user then expels the mouthwash from the mouth.

It is an object the mouthwash embodiment of the present invention to provide a solution which can clean areas of the teeth and gums which cannot be reached with floss or a toothbrush. A further object of the present invention is to provide an dentifrice to inhibit the bacteria which grow on plaque. Yet another object of the present invention is to provide a mouthwash and toothpaste that can help control bad breath. Another object of the present invention is to provide a dentifrice which includes natural constituents and does not cause the side effects of alcohol-based mouthwashes.

DESCRIPTION

To combat gum disease, a dentifrice, optionally in the form of either a mouthwash solution or a toothpaste, is provided which will assist in killing the bacteria which cause gingivitis as well as reduce swelling and inflammation of the gums. The dentifrice includes natural constituents such as nutrients and herbal supplements. Specifically, the present invention contemplates the use of natural constituents which foster wound repair and cell reproduction to assist the body in healing, repairing, and replacing gum tissue damaged by the bacteria and the infection caused thereby. Also, the present invention contemplates the use of natural constituents which boost immunity to assist the body in fighting, and preventing, infection of the gum tissue and teeth. Additionally, the present invention contemplates the use of natural constituents which reduce inflammation to ease the pain and sensitivity of the gum tissue and teeth as well as encourage healing. Further, the present invention contemplates the use of natural constituents which have anti-bacterial properties to inhibit, or assist the body in inhibiting, the bacteria in the plaque. It is believed that a synergistic effect occurs when one or more nutrients is combined with one or more herbal agents in an aqueous solution.

As medical professionals reexamine natural remedies, it is becoming apparent that a variety of nutrients meet the criteria described above; that is, many nutrients can aid in cell reproduction, immunity, and wound repair while inhibiting inflammation and bacterial growth. Among those nutrients which are believed to provide these benefits are folic acid, zinc, calcium, coenzyme Q10, bioflavonoids, and vitamin C. The present invention includes at least one of these nutrients. While any of these nutrients could be used, in an optional embodiment, the present invention includes the nutrients folic acid and zinc which may be absorbed through the gums while the user is using the dentifrice.

Folic acid is important to DNA synthesis and, consequently, cell reproduction. It is also known in the art that folic acid reduces gum inflammation and bleeding, as well as binding to toxins secreted by bacteria in plaque. In an optional embodiment, the present invention includes approximately 10% by mass folic acid. On a dosage basis, one must look to the recommended daily allowance. According to the National Research Council Recommended Dietary Allowance, adults require between 0.18 and 0.2 milligrams of folic acid. Moreover, adverse effect may be caused by an excess of folic acid. Thus, the quantity of folic acid in the present invention must be such that less than 0.2 milligrams of folic acid are absorbed through the gums during use. In an optional embodiment, a 5 milliliter dose of the present invention includes approximately 0.5 milligrams of folic acid because not all of the folic acid in the mouthwash will be absorbed through the gums.

Similarly, zinc is known in the art to be important to cell reproduction, wound repair, and immunity. Zinc is also known to have anti-bacterial properties. In an optional embodiment, the present invention includes approximately 10% by mass zinc. Again, on a dosage basis, one must look to the recommended daily allowance. According to the National Research Council Recommended Dietary Allowance, adults require between 12 and 15 milligrams of zinc. Moreover, an excess of zinc may result in adverse effects. Thus, quantity of zinc in the present invention must be such that less than 15 milligrams of zinc are absorbed through the gums during use. In an optional embodiment, a 5 milliliter dose of the present solution includes approximately 0.5 milligrams of zinc.

There are also a variety of herbal agents which are known to promote immunity and have anti-inflammatory and anti-bacterial properties such as myrrh oil, clove oil, chamomile, echinacea, and sanguinarine. The present invention includes at least one of these herbal agents. While any of these herbal supplements could be used, in an optional embodiment, the present invention includes myrrh oil and clove oil.

Myrrh is known to relieve inflamed tissues. Also, myrrh is known in the art to kill bacteria and stimulate the activity of white cells. Further, myrrh has a pleasant aroma which can help control bad breath odors. While any quantity of myrrh oil could be used, in an optional embodiment, the present invention includes approximately 25% by mass myrrh oil. Thus, a 5 milliliter dose of the present invention includes approximately 1.25 milligrams myrrh oil.

Clove oil is known to have anti-bacterial and anti-inflammatory properties. Also, like myrrh, clove oil has a pleasant aroma which can help control bad breath odors. While any quantity of clove oil could be used, in an optional embodiment, the present invention includes approximately 25% by mass clove oil. Thus, a 5 milliliter dose of the present invention includes approximately 1.25 milligrams clove oil.

Because of the known side effects of using alcohol-based dentifrices, the dentifrice of the present invention includes water rather than alcohol. Optionally, the water is distilled water. Thus, in the optional mouthwash embodiment of the present invention, the balance of the mouthwash solution is made up of water. In an optional mouthwash solution embodiment, the mouthwash solution includes approximately 30% by mass water. This means that a 5 milliliter dose of the present invention includes approximately 1.5 milliliters of water. The toothpaste of the present invention may additionally include a thickening agent or other means for suspending the active constituents to create a paste-like consistency.

The quantities and percentages of constituents described above are for an optional embodiment and may be varied. The amount of variation is limited only by the known side effects of an excess of nutrients. That is, one may vary the quantities so long as the quantity is kept below those quantities which are known to cause side effects. The quantities and percentages of constituents of an optional embodiment of the present invention are summarized in Table 1 below:

TABLE 1

| Constituent | Percentage by mass | Mass per 5 ml dose |
|---|---|---|
| Folic acid | 10% | 0.5 mg |
| Zinc | 10% | 0.5 mg |
| Myrrh oil | 25% | 1.25 mg |
| Clove oil | 25% | 1.25 mg |
| Water | 30% | 1.5 mg |

To create the solution of the present invention, the constituents are combined at ambient pressure and room temperature. Zinc is added as a powder and folic acid, myrrh oil and clove oil are added as liquids in the proportions described above. The balance of the mouthwash solution is water. The toothpaste embodiment may additionally include a thickening agent.

To use the toothpaste embodiment of the present invention, the user uses the toothpaste with a toothbrush in a manner known in the art. To use the mouthwash of the present invention, the user first brushes and flosses the user's teeth. This removes food particles from the teeth and gums. Also, this loosens or removes plaque. The user then pours a single dose of the present invention into the user's mouth and swishes the solution in the user's mouth. In an optional embodiment, a single dose is 5 milliliters. As the user swishes the solution, the user swishes with full strength around and through the teeth for approximately thirty to sixty seconds. The user then expels the solution from the mouth and rinses the user's mouth with water. Preferably, the solution is not swallowed. Rather, absorption of the nutrients takes place through the gum tissue as the solution is swished.

In an optional embodiment, the present invention is used each time the user flosses and brushes the teeth. Thus, in an optional embodiment, the user uses the dentifrice at least twice per day. Also, the present invention is used in conjunction with regular professional dental cleanings.

It is an advantage of the present invention that the mouthwash solution embodiment can clean areas of the teeth and gums which cannot be reached with floss or a toothbrush because the mouthwash embodiment is a liquid which may be swished through the teeth. A further advantage of the present invention is that the dentifrice inhibits bacterial growth because of the anti-bacterial properties of the constituents. Yet another advantage of the present invention that the dentifrice of the present invention can help control bad breath because clove oil and myrrh have pleasant aromas and also inhibit bacteria growth. Another advantage of the present invention is that it provides a dentifrice which includes natural constituents, such as nutrients and herbal supplements, and includes water rather than alcohol.

What is claimed is:

1. A non-alcoholic, water-based dentifrice for cleaning a user's mouth, comprising:

folic acid in an amount of substantially 10% of the total mass of the dentifrice;

zinc in an amount of substantially 10% of the total mass of the dentifrice;

clove oil in an amount of substantially 25% or more of the total mass of the dentifrice;

myrrh oil in an amount of substantially 25% or more of the total mass of the dentifrice; and water.

2. The dentifrice of claim 1 further comprising a thickening agent to form a toothpaste.

3. A non-alcoholic, water-based mouthwash solution for cleaning a user's mouth, comprising:

folic acid in an amount of substantially 10% of the total mass of the mouthwash solution;

zinc in an amount of substantially 10% of the total mass of the mouthwash solution;

clove oil in an amount of substantially 25% of the total mass of the mouthwash solution;

myrrh oil in an amount of substantially 25% of the total mass of the mouthwash solution; and water in an amount of substantially 30% of the total mass of the mouthwash solution.

4. A process for making a non-alcoholic, water-based mouthwash solution for rinsing a user's mouth, comprising:

combining powdered zinc in an amount of substantially 10% of the total mass of the mouthwash solution, liquid folic acid in an amount of substantially 10% of the total mass of the mouthwash solution, liquid myrrh oil in an amount of substantially 25% or more of the total mass of the mouthwash solution, liquid clove oil in an amount of substantially 25% or more of the total mass of the mouthwash solution, and liquid water as the balance of the mouthwash solution at ambient temperature and pressure.

5. A product made according to the process of claim 4.

* * * * *